US012201600B2

(12) United States Patent
Wickenhauser et al.

(10) Patent No.: US 12,201,600 B2
(45) Date of Patent: *Jan. 21, 2025

(54) TREATMENT OF HERPES ZOSTER WITH TOPICAL TETRACAINE

(71) Applicant: PAGARI LIFE SCIENCE CORP, Bethalto, IL (US)

(72) Inventors: Alan J Wickenhauser, Moro, IL (US); Stephen E Peipert, Edwardsville, IL (US)

(73) Assignee: PAGARI LIFE SCIENCE CORP

( * ) Notice: Subject to any disclaimer, the term of this patent is extended or adjusted under 35 U.S.C. 154(b) by 0 days.

This patent is subject to a terminal disclaimer.

(21) Appl. No.: 18/068,403

(22) Filed: Dec. 19, 2022

(65) Prior Publication Data

US 2024/0197669 A1    Jun. 20, 2024

(51) Int. Cl.
*A61K 31/245*    (2006.01)
*A61K 47/10*    (2017.01)
*A61P 31/22*    (2006.01)

(52) U.S. Cl.
CPC ............ *A61K 31/245* (2013.01); *A61K 47/10* (2013.01); *A61P 31/22* (2018.01)

(58) Field of Classification Search
CPC ........ A61K 31/245; A61K 47/10; A61P 31/22
See application file for complete search history.

(56) References Cited

U.S. PATENT DOCUMENTS

| 5,696,160 A | 12/1997 | Miller et al. |
| 8,263,047 B2 | 9/2012 | Wickenhauser et al. |
| 8,623,334 B1 | 1/2014 | Wickenhauser et al. |
| 8,968,710 B1 | 3/2015 | Wickenhauser et al. |

FOREIGN PATENT DOCUMENTS

| CN | 1221264 C | 10/2005 | |
| CN | 114209720 A | 3/2022 | |
| WO | WO-2011028629 A1 * | 3/2011 | ........... A61K 31/167 |
| WO | WO-2012064766 A2 * | 5/2012 | ....... A61F 13/00063 |

OTHER PUBLICATIONS

Riopelle et al. "Treatment of the cutaneous pain of acute herpes zoster with 9% lidocaine (base) in petrolatum/paraffin ointment," J. American Academy of Dermatology, 1994, vol. 30, Issue 5, Part 1, pp. 757-767 (Year: 1994).*
Daiki Yamanaka, et al. Peripheral nerve block with a high concentration of tetracaine dissolved in bupivacaine for intractable post-herpetic itch: a case report, Yamanaka et al. JA Clinical Reports (2016) 2:43.
Christa Hopp, et al., Clinical efficacy of tetracaine anesthetic paste, Gen Dent, Mar-Apr. 2012, 60(2):e69-73, abstract only.
Bradley Carn, et al., Achieving pulpal anesthesia with a topical anesthetic paste, Journal of Orofacial Sciences, 2015, 7:2:125-128.

(Continued)

*Primary Examiner* — Umamaheswari Ramachandran
(74) *Attorney, Agent, or Firm* — DUANE MORRIS LLP

(57) ABSTRACT

The present invention relates to a method of treating herpes zoster (shingles), such as in the acute eruptive phase, comprising topically administering tetracaine base (or a pharmaceutically acceptable salt thereof) to a patient in need of such treatment.

20 Claims, 3 Drawing Sheets

(56) References Cited

OTHER PUBLICATIONS

Lewis H. Kaminester, et al., A Double-blind, Placebo-controlled Study of Topical Tetracaine in the Treatment of Herpes Labialis, J. Am. Acad Dermatol, May 17, 1999, 41:6:996-1001.
Lidocaine and Tetracaine Cream to Treat Postherpetic Neuralgia (PHN), NCT00609323, ClinicalTrials.gov, Oct. 29, 2022 (6 pages).
K.J. Miller, et al. In Vitro Transdermal Diffusional Properties of Tetracaine from a Topical Formulation, 21 pages.
K.J. Miller, et al., Solubility and in vitro Percutaneous Absorption of Tetracaine from Solvents of Propylene Glycol and Saline, International Journal of Pharmaceutics, 1993, 98:101-111.
International Search Report and Written Opinion in International Patent Application No. PCT/US2023/084790, dated Apr. 5, 2024, in 14 pages.

\* cited by examiner

TREATMENT OF HERPES ZOSTER WITH TOPICAL TETRACAINE

FIELD OF THE INVENTION

The present invention relates to a method of treating herpes zoster (shingles) comprising topically administering tetracaine base (or a pharmaceutically acceptable salt thereof) to a patient in need of such treatment.

BACKGROUND OF THE INVENTION

Approximately one million people in the United States are diagnosed with shingles, herpes zoster, each year. This viral disease is premised by a primary infection with varicella zoster (chicken pox) and is caused by a reactivated replication of a dormant virus that resides in ganglionic nerves.

The risk of shingles increases with age, and individuals with compromised immune systems may be particularly vulnerable. The disease comprises three phases: a pre-eruptive phase characterized by a multitude of sensory nerve phenomena, which may last 48-72 hours; an acute eruptive phase characterized by lesions, mild to severe pain, pruritus, and hyperesthesia, which may last 2-4 weeks; and a chronic phase characterized by post-herpetic neuralgia (PHN), which may persist 3-6 months or longer and may affect approximately 20% of shingles patients.

Two zoster vaccines have been approved in the United States. Shingrix, marketed by GlaxoSmithKline, is a recombinant subunit vaccine which has been used in many countries since 2017. Shingrix is a suspension for intramuscular injection indicated for the prevention of herpes zoster in adults aged 50 years and older, and in adults aged 18 years or older who are or will be at increased risk of herpes zoster due to immunodeficiency or immunosuppression caused by known disease or therapy. The Shingrix vaccine has various side effects such as pain at the injection site, redness, swelling, muscle pain, fatigue, and a possibility of causing Guillain Barré Syndrome (which FDA required a warning of in 2021).

Zostavax (Merck), in use since 2006, is an attenuated vaccine which consists of a larger-than-normal dose of chickenpox vaccine. Zostavax was discontinued in the United States in November 2020.

Tetracaine, also known as amethocaine, is an ester local anesthetic used to numb the eyes, nose, or throat. It may also be applied to the skin before starting an intravenous (injection) to decrease pain from the procedure.

U.S. Pat. Nos. 8,263,047, 8,623,334, and 8,968,710 disclose a topical anesthetic for dental procedures containing about 3 wt. % to 10 wt. % tetracaine in a vehicle suitable for administration to the oral mucosa. Kaminester et al., J. Am. Acad. Dermatol., 41(6), 996-1001, 1999, describes the result of a double blind, placebo-controlled study of topical tetracaine in the treatment of herpes labialis. Yamanaka et al., JA Clinical Reports, 2(43), 1-4, 2016, describes a case report study of peripheral nerve block using tetracaine dissolved in bupivacaine for intractable post-herpetic itch. Pliaglis®, a topical cream containing lidocaine and tetracaine (7%/7%), is indicated for use on intact skin in adults to provide topical local analgesia for superficial dermatological procedures such as dermal filler injection, pulsed dye laser therapy, facial laser resurfacing, and laser-assisted tattoo removal, and has been studied for the treatment of postherpetic neuralgia (PHN) (NCT00609323).

There is a need for new methods and compositions for the treatment and/or prevention of herpes zoster, for example, methods that do not involve intramuscular injection. The present invention addresses such needs.

SUMMARY OF THE INVENTION

The present inventor has surprisingly found that topical administration of tetracaine base is effective in the treatment of herpes zoster (shingles), including its active eruptive phase. One advantage of the methods described herein is that they avoid the need for the existing vaccines which have side effects including an elevated risk of Guillain Barré Syndrome.

One embodiment is a method of treating herpes zoster in a patient in need thereof (such as a patient in the active eruptive phase of herpes zoster) by topically administering to the patient a composition comprising from about 2 wt. % to about 10 wt. % of tetracaine base (or a pharmaceutically acceptable salt thereof such as tetracaine hydrochloride), based on the 100% total weight of the composition. In one embodiment, the patient is in the active eruptive phase of herpes zoster when initially administered the composition.

Another embodiment is a method of treating herpes zoster in the active eruptive phase in a patient in need thereof by topically administering to the patient a composition comprising from about 2 wt. % to about 10 wt. % of tetracaine base (or a pharmaceutically acceptable salt thereof such as tetracaine hydrochloride), based on the 100% total weight of the composition.

Yet another embodiment is a method of treating lesions associated with herpes zoster in the active eruptive phase in a patient in need thereof by topically administering to the patient a composition comprising from about 2 wt. % to about 10 wt. % of tetracaine base (or a pharmaceutically acceptable salt thereof such as tetracaine hydrochloride), based on the 100% total weight of the composition.

Yet another embodiment is a method of treating one or more symptoms associated with herpes zoster in the active eruptive phase in a patient in need thereof comprising topically administering to the patient a composition comprising from about 2 wt. % to about 10 wt. % of tetracaine base (or a pharmaceutically acceptable salt thereof such as tetracaine hydrochloride), based on the 100% total weight of the composition. The one or more symptoms can be selected from lesions, blisters, rash, mild to severe pain, pruritus, hyperesthesia, and any combination of any of the foregoing. In one embodiment, the symptom treated is lesions. In another embodiment, the symptom treated is blisters. In yet another embodiment, the symptom treated is rash.

In one embodiment, the method comprises topically administering a composition comprising between about 3% and about 10% by weight of tetracaine base (or a pharmaceutically acceptable salt thereof such as tetracaine hydrochloride).

In one embodiment of any of the methods described herein, the composition comprises about 2 wt. % to about 10 wt. % of tetracaine base. In one embodiment of any of the methods described herein, tetracaine base is the sole active ingredient in the composition. In one embodiment of any of the methods described herein, the composition does not contain lidocaine or bupivacaine.

In one embodiment of any of the methods described herein, the only form of tetracaine included in the composition is tetracaine base.

In one embodiment of any of the methods described herein, the composition comprises about 2 wt. % to about 10 wt. % of tetracaine hydrochloride.

In certain embodiments of any of the methods described herein, the composition comprises a penetration enhancer (such as propylene glycol), one or more mucoadhesives, and a non-aqueous vehicle (such as a hydrocarbon gel). The composition optionally further comprises a thickening agent and/or an odor masking agent.

In certain embodiments of any of the methods described herein, the composition comprises a carrier comprising a non-aqueous vehicle. In certain embodiments of any of the methods described herein, the non-aqueous vehicle comprises a high molecular weight poly(ethylene oxide) homopolymer, a cellulose polymer, propylene glycol and a plasticized hydrocarbon gel.

In certain embodiments of any of the methods described herein, the poly(ethylene oxide) homopolymer has a molecular weight about 4,000,000 Daltons (g/mol).

In certain embodiments of any of the methods described herein, the poly(ethylene oxide) is present in an amount of about 5 wt. % and the cellulose polymer is sodium carboxymethylcellulose and is present in an amount of about 4 wt. %.

In certain embodiments of any of the methods described herein, the propylene glycol is present in an amount of about 5 wt. % to about 15 wt. %.

In certain embodiments of any of the methods described herein, the composition comprises between about 2% and about 6% by weight of tetracaine base.

In certain embodiments of any of the methods described herein, the composition comprises about 2% by weight of tetracaine base.

In certain embodiments of any of the methods described herein, the composition comprises about 6% by weight of tetracaine base.

In certain embodiments of any of the methods described herein, the patient is suffering from herpes zoster in the acute phase.

In certain embodiments of any of the methods described herein, the composition is topically applied up to three times a day, e.g., once a day, twice a day or three times a day.

In certain embodiments of any of the methods described herein, the patient sees improvement in the symptoms of herpes zoster within about 7 days, within about 5 days or within about 4 days.

In certain embodiments of any of the methods described herein, the patient sees improvement in the symptoms of herpes zoster in less than about 7 days, such as in six days, in five days, or in four days.

DETAILED DESCRIPTION OF THE INVENTION

Figure 1:
FIG. 1 shows the face of the patient described in Example 3 prior to treatment (Day 0) and on Days 1-5 and 7 of treatment with the topical composition of Example 1.

Tetracaine is a white, or light yellow, waxy solid melting in the range of 41° C. to 46° C. It is very slightly soluble in water, and soluble in alcohol, ether, benzene and chloroform.

In certain embodiments of any of the methods descried herein, the tetracaine is provided in base form, i.e., not as a pharmaceutically acceptable salt, such as the hydrochloride salt.

In certain embodiments of any of the methods descried herein, the concentration of the tetracaine is from about 2 or 3 wt. % to about 10 wt. % of the total composition, such as from about 2 wt. % to about 6 wt. % of the total composition, e.g., to deliver an effective dosage. In another embodiment of any of the methods descried herein, the concentration of the tetracaine is about 2 wt. % of the total composition. In yet another other embodiment of any of the methods descried herein, the concentration of the tetracaine is about 6 wt. %.

In certain embodiments of any of the methods descried herein, one or more mucoadhesives is included in the composition. As used herein the term mucoadhesive means a natural or synthetic substance, e.g., gels, pastes, macromolecules, polymers, and oligomers, or mixtures thereof, that can adhere to a subject's mucous membrane for a period of time sufficient to locally deliver a therapeutically effective amount of tetracaine. The composition itself need not be mucoadhesive, as long as it can form a mucoadhesive upon on the contact with the mucosa.

Examples of mucoadhesives for use in any of the compositions described herein include, but are not limited to, pectin, alginic acid, chitosan, hyaluronic acid, polysorbates, such as polysorbate-20, -21, -40, -60, -61, -65, -80, -81, -85; polyethylene glycol, such as PEG-7, -14, -16, -18, -55, -90, -100, -135, -180, -4, -240, -6, -8, -9, -10, -12, -20, or -32; oligosaccharides and polysaccharides, such as gellan, carrageenan, xanthan gum, gum arabic, and dextran; cellulose esters and cellulose ethers; modified cellulose polymers, such as carboxymethylcellulose, sodium carboxymethylcellulose, hydroxyethylcellulose, hydroxypropyl methylcellulose, hydroxyethyl ethylcellulose; polyether polymers and oligomers, such as polyoxyethylene; condensation products of polyethylene oxide with various reactive hydrogen containing compounds having long hydrophobic chains, such as condensation products of poly(ethylene oxide) with fatty acids, fatty alcohols, fatty amides, or polyhydric alcohols; polyether compounds, such as poly(methyl vinyl ether), or polyoxypropylene of less than 10 repeating units; polyether compounds, such as block copolymers of ethylene oxide and propylene oxide; ORABASE7 (a mixture of gelatine, pectin and sodium carboxymethyl cellulose in a plasticized hydrocarbon gel, commercially available from Hoyt laboratories, Needham, Mass.), or any combination of any of the foregoing.

In certain embodiments of any of the compositions described herein, the mucoadhesive is water soluble and a combination of mucoadhesives is used. For example, homopolymers of ethylene oxide in combination with a second mucoadhesive such as sodium carboxymethylcellulose. Commercially available homopolymers of ethylene oxide are sold under the trademark POLYOX by Dow Chemical Company, Midland, Mich. POLYOX poly(ethylene oxide) polymers have a number of properties for mucoadhesion—namely, water solubility, hydrophilicity, high molecular weight, hydrogen bonding functionality, and good biocompatibility. The polymers have a long linear chain structure which allows them to form a strong interpenetrating network with mucus. In one preferred embodiment, the mucoadhesive includes poly(ethylene oxide) polymers with a molecular weight of 4,000,000 Daltons and higher. The amount of mucoadhesive in the formulation depends upon the mucoadhesives selected and the consistency desired in the composition.

In one embodiment of any of the compositions described herein, the composition comprises sodium carboxymethyl cellulose. In certain embodiments of any of the compositions described herein, the composition comprises between about 1 wt. % and about 10 wt. % sodium carboxymethyl cellulose or between about 3 wt. % and about 5 wt. % sodium carboxymethyl cellulose. In certain embodiments of any of the compositions described herein, the composition comprises between about 4 wt. % sodium carboxymethyl cellulose.

In one embodiment of any of the compositions described herein, the composition comprises POLYOX WSR 301 (a water-soluble, nonionic poly(ethylene oxide) polymer with a molecular weight of 4,000,000 Daltons (g/mol) (available from DuPont) in combination with sodium carboxymethylcellulose (medium viscosity). In one embodiment, the sodium carboxymethylcellulose having medium viscosity has a viscosity in a 2% solution in water at 25° C. of 400-800 cps. In this embodiment, the combined mucoadhesive comprises up to about 10 wt. %, such as about 9 wt. %, of the composition, with POLYOX WSR 301 comprising about 3 wt. % to about 8 wt. %, such as about 5 wt. % of the composition and sodium carboxymethylcellulose comprising about 2 wt. % to about 5 wt. %, such as about 4 wt. % of the composition. In the absence of a mucoadhesive like POLYOX WSR 301, the topical adhesive tends to migrate from the site of application, spreading the therapeutic action of the tetracaine to unintended areas.

In one embodiment of any of the compositions described herein, the composition comprises propylene glycol, for example, as a penetration enhancer to increase the absorption of the tetracaine into the mucosa. Other suitable penetration enhancers may be included. The penetration enhancers should be physicochemically stable and not have pharmacologic effects and preferably should not have disagreeable smell, color or taste. Without limitation, in addition to propylene glycol, other glycols, monohydric alcohols, and fatty acid glycerides may also serve as penetration enhancers. In one embodiment, any of the compositions described herein does not include glycerin.

In one embodiment of any of the compositions described herein, the propylene glycol is present in an amount from about 5 wt. % to 15 wt. %.

In one embodiment of any of the compositions described herein, when the poly (ethylene oxide) homopolymer (such as POLYOX WSR 301) is present in an amount of about 5 wt. % and the sodium carboxymethylcellulose is present in an amount of about 4 wt. %, the propylene glycol may be present in an amount of about 10 wt. % as larger amounts of propylene glycol may render the paste too fluid to stay in place at the site of application.

In one embodiment, a plasticized hydrocarbon gel completes the carrier vehicle for tetracaine in any of the compositions described herein. The plasticized hydrocarbon gel may be mixture of polyethylene in mineral oil, such as light mineral oil (e.g., Jelene, available from Fagron, Inc.). The plasticized hydrocarbon gel keeps the paste from dissolving away quickly, giving tetracaine time to penetrate. In one embodiment of any of the compositions described herein, the plasticized hydrocarbon gel makes up about 70 wt. % to about 80 wt. %, such as about 75 wt. % or about 79 wt. %, of the composition.

In one embodiment, any of the compositions described herein may include one or preservatives. Preferably, if present, the preservative comprises no more than about 1 wt. % but may vary depending on the other components.

In one embodiment, any of the compositions described herein may include one or more odor masking agents. Suitable odor masking agents include, but are not limited to, peppermint oil, In one embodiment of any of the compositions described herein, the odor masking agent (such as peppermint oil) makes up about 0.1 wt. % to about 1 wt. %, such as about 0.6 wt. % to about 0.7 wt. %, of the composition.

In one embodiment, any of the compositions described herein has a pH of between about 8 and about 10, such as between 8.5 and about 9.5, such as about 9.

In one embodiment, the composition contains (a) from about 2 wt % to about 10 wt % of tetracaine base, (b) from about 2 to about 8 wt % sodium carboxymethyl cellulose, (c) from about 2 to about 10 wt % of polyethylene oxide (preferably having a molecular weight ranging from about 2,000,000 to about 6,000,000 Daltons), (d) from about 5 to about 15 wt % propylene glycol, (e) from about 65 to about 85 wt % plasticized base (such as a base comprising from about 92 to about 98 wt % mineral oil and about 2 to about 8 wt % polyethylene), and optionally (f) about 0.4 to about 1.0 wt % peppermint oil. Preferably, the sodium carboxymethyl cellulose has a viscosity in a 2% solution in water at 25° C. of 400-800 cps. In one preferred embodiment, the composition contains (a) from about 6 wt % of tetracaine base, (b) about 4 wt % sodium carboxymethyl cellulose, (c) about 5 wt % of polyethylene oxide (preferably having a molecular weight ranging from about 2,000,000 to about 6,000,000 Daltons), (d) about 10 wt % propylene glycol, (e) about 74 wt % plasticized base (such as a base comprising about 95 wt % mineral oil and about 5 wt % low molecular weight polyethylene), and optionally (f) about 0.7 wt % peppermint oil.

The topical anesthetic compositions of the present invention may be prepared using ordinary production methods. In one embodiment, the composition is prepared as described in Example 1.

The compositions may include the excipients and be prepared by the methods described in U.S. Pat. Nos. 8,263,047, 8,623,334, and 8,968,710, which are hereby incorporated by reference.

EXAMPLES

Example 1

A topical composition containing 6 wt. % tetracaine base having the formulation shown in the table below was prepared by mixing the appropriate components in the specified amounts.

| INGREDIENT | WEIGHT (% w/w) |
| --- | --- |
| Tetracaine USP Base | 6.0 |
| Sodium Carboxymethylcellulose USP, medium viscosity | 4.0 |
| PolyOx WSR 301 | 5.0 |
| Propylene Glycol USP | 10.0 |
| Plasticized Base (Jelene) (95% mineral oil and 5% low molecular weight polyethylene) | 74.33 |
| Peppermint Oil, NF | 0.67% |

The topical composition can be prepared as follows. Sodium carboxymethyl cellulose, PolyOx WSR 301, and tetracaine are ground in separate glass mortars to a fine powder and set aside. Ten percent extra tetracaine is weighed out because some of the tetracaine may adhere to the mortar. By starting with 10% extra, the ground tetracaine available for transfer results in a 6 wt. % composition.

Plasticized base (Jelene) is placed in a 200 ml beaker and the beaker placed directly onto a hotplate. The temperature of the hot plate is set on its lowest position. The plasticized base is gently heated until it became soft and semi-fluid. At which point, the plasticized base is workable for compounding purposes. plasticized base melts at about 82° F. Heating is stopped before the plasticized base totally melts as separation may occur and plasticized base may not resume its original consistency when cooled.

The ground sodium carboxymethylcellulose is added in small portions to the heated plasticized base with stirring after each addition to ensure a uniform mix. The beaker is removed from the heat and the mixture allowed to cool.

On an ointment slab, a portion of the finely ground tetracaine is worked with propylene glycol (25% of the total propylene glycol). The tetracaine and propylene glycol mixture is combined with a portion of plasticized base via geometric dilution. The cooled plasticized base and sodium carboxymethylcellulose mixture is then worked into the tetracaine, propylene glycol (25% of the total propylene glycol) and plasticized base mixture via geometric dilution.

In a glass mortar, the ground PolyOx WSR 301 is wetted with propylene glycol (75% of the total propylene glycol).

The Polyox WSR 301 and propylene glycol mixture is then incorporated via geometric dilution with the other ingredients previously mixed together on the ointment slab to form the topical paste.

Example 2

A topical composition containing 2 wt. % tetracaine base having the formulation shown in the table below was prepared by mixing the appropriate components in the specified amounts. This composition can be prepared as described in Example 1.

| INGREDIENT | WEIGHT (% w/w) |
| --- | --- |
| Tetracaine USP Base | 2.0 |
| Sodium Carboxymethylcellulose USP, medium viscosity | 4.0 |
| PolyOx WSR 301 | 5.0 |
| Propylene Glycol USP | 10.0 |
| Plasticized Base (Jelene) | 78.33 |
| Peppermint Oil, NF | 0.67 |

Example 3

A 31 year old female patient presented with shingles in the active eruptive phase on her face, in her mouth, and on her cornea. The patient was currently taking 3 eye medications and valacyclovir (Valtrex). The patient was topically administered the topical composition of Example 1 three times a day. After seven days, the shingles was almost resolved and the patient had no pain. FIG. 1 shows the face of the patient prior to treatment (Day 0) and on Days 1-5 and 7 of treatment with the topical composition of Example 1.

Example 4

A 10 year old male patient presented with shingles on his arms. The patient was topically administered the topical composition of Example 1 three times a day. After five days, the shingles was almost completely resolved.

Figure 2A:
FIG. 2A shows the arms of the patient described in Example 4 at Day 0, prior to treatment with topical administration with the topical composition of Example 1.
Figure 2B:
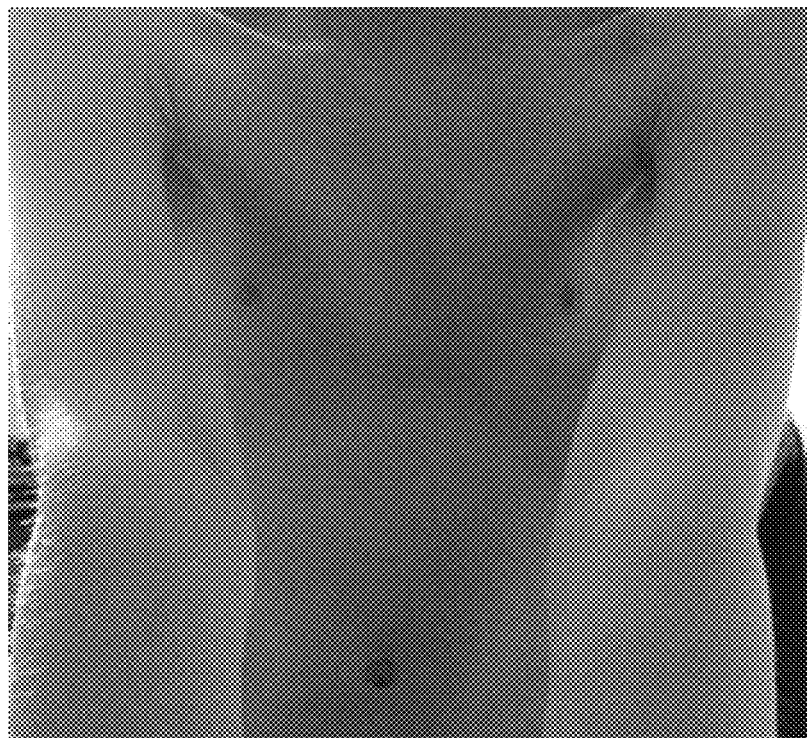
FIG. 2B shows the arms of the patient described in Example 4 after administration of the topical composition of Example 1 three times a day for five days.

FIG. 2A shows the arms of the patient at Day 0 (prior to treatment). FIG. 2B shows the arms of the patient after administration of the topical composition of Example 1 three times a day for five days.

Example 5

A 57 year old female patient presents with severe blisters on the left torso. The patient was topically administered the topical composition of Example 1 three times a day. Upon applying the topical composition of Example 1, the patient immediately felt no pain. After four days, the shingles was completely resolved.

Example 6

An 83 year old female patient presents with severe blisters on the left torso and in great pain. The patient was taking an antiviral and pain medication (acyclovir and oxycodone). The patient was then topically administered the topical composition of Example 1 three times a day. Upon applying the topical composition of Example 1, the patient immediately felt no pain. After seven days, the shingles was completely resolved.

All references (including patents, patent applications, and literature) cited herein are hereby incorporated by reference in their entireties.

What is claimed is:

1. A method of reducing the number of blisters in a patient having herpes zoster in the active eruptive phase comprising topically administering to the patient a composition comprising (i) from about 2 wt. % to about 10 wt. % of tetracaine base or a pharmaceutically acceptable salt thereof, based on the 100% total weight of the composition, wherein an effective amount of the composition is administered to reduce the number of blisters in said patient having herpes zoster in the active eruptive phase,
   wherein the administering is performed each day for one to seven contiguous days and
   wherein tetracaine base is the sole active ingredient in the composition.

2. The method of claim 1, wherein the composition comprises from about 2 wt. % to about 6 wt. % of tetracaine base.

3. The method of claim 1, wherein the composition comprises a carrier comprising a non-aqueous vehicle.

4. A method of reducing the number of blisters in a patient having herpes zoster in the active eruptive phase comprising topically administering to the patient a composition comprising from about 2 wt. % to about 10 wt. % of tetracaine base, based on the 100% total weight of the composition, wherein the composition comprises a carrier comprising a non-aqueous vehicle, and the non-aqueous vehicle comprises a high molecular weight poly(ethylene oxide) homopolymer, a cellulose polymer, propylene glycol and a plasticized hydrocarbon gel,
   wherein the administering is performed each day for one to seven contiguous days, and
   wherein tetracaine base is the sole active ingredient in the composition.

5. The method of claim 4, wherein the poly(ethylene oxide) homopolymer has a molecular weight of about 4,000,000 daltons.

6. The method of claim 4, wherein the poly(ethylene oxide) homopolymer is present in an amount of about 5 wt.

% and the cellulose polymer is sodium carboxymethylcellulose and is present in an amount of about 4 wt. %.

7. The method of claim 4, wherein the propylene glycol is present in an amount of about 5 wt. % to about 15 wt. %.

8. The method of claim 1, wherein the composition comprises about 2 wt. % of tetracaine base.

9. The method of claim 1, wherein the composition comprises about 6 wt. % of tetracaine base.

10. The method of claim 1, wherein the composition is topically applied up to three times a day.

11. The method of claim 3, wherein the non-aqueous vehicle comprises a high molecular weight poly(ethylene oxide) homopolymer, a cellulose polymer, propylene glycol and a plasticized hydrocarbon gel.

12. The method of claim 11, wherein the poly(ethylene oxide) homopolymer has a molecular weight of about 4,000,000 daltons.

13. The method of claim 11, wherein the poly(ethylene oxide) homopolymer is present in an amount of about 5 wt. % and the cellulose polymer is sodium carboxymethylcellulose and is present in an amount of about 4 wt. %.

14. The method of claim 11, wherein the propylene glycol is present in an amount of about 5 wt. % to about 15 wt. %.

15. The method of claim 1, wherein the administering is performed one, two, or three times per day.

16. The method of claim 4, wherein the administering is performed one, two, or three times per day.

17. The method of claim 1, wherein the administering is performed each day for four contiguous days.

18. The method of claim 1, wherein the administering is performed each day for five contiguous days.

19. The method of claim 4, wherein the administering is performed each day for four contiguous days.

20. The method of claim 4, wherein the administering is performed each day for five contiguous days.

* * * * *